(12) United States Patent
Wallace (10) Patent No.: US 12,390,099 B2
(45) Date of Patent: Aug. 19, 2025

(54) COLPOSCOPE WITH INTEGRATED PATIENT MANAGEMENT AND THERMAL ABLATION FUNCTIONALITY

(71) Applicant: William Dean Wallace, Lehi, UT (US)

(72) Inventor: William Dean Wallace, Lehi, UT (US)

(73) Assignee: Liger Medical LLC, Lehi, UT (US)

( * ) Notice: Subject to any disclaimer, the term of this patent is extended or adjusted under 35 U.S.C. 154(b) by 0 days.

(21) Appl. No.: 17/838,125

(22) Filed: Jun. 10, 2022

(65) Prior Publication Data

US 2023/0397806 A1 Dec. 14, 2023

(51) Int. Cl.
| | | |
|---|---|---|
| A61B 1/303 | (2006.01) | |
| A61B 1/00 | (2006.01) | |
| A61B 1/018 | (2006.01) | |
| A61B 1/05 | (2006.01) | |
| A61B 1/06 | (2006.01) | |
| A61B 18/00 | (2006.01) | |
| A61B 18/04 | (2006.01) | |
| G16H 30/20 | (2018.01) | |

(52) U.S. Cl.
CPC .......... *A61B 1/303* (2013.01); *A61B 1/00052* (2013.01); *A61B 1/018* (2013.01); *A61B 1/05* (2013.01); *A61B 1/0676* (2013.01); *A61B 18/04* (2013.01); *G16H 30/20* (2018.01); *A61B 2018/00559* (2013.01); *A61B 2018/00577* (2013.01)

(58) Field of Classification Search
CPC .. A61B 1/303; A61B 1/32; A61B 2018/00559
See application file for complete search history.

(56) References Cited

U.S. PATENT DOCUMENTS

| 10,849,675 B2 | 12/2020 | Wallace | |
|---|---|---|---|
| 2022/0000339 A1* | 1/2022 | Nwanna-Nzewunwa | ................... |
| | | | G16H 40/63 |
| 2024/0065540 A1* | 2/2024 | Commuri | .............. G06T 7/0012 |

OTHER PUBLICATIONS

"Computer Aided Cervical Mapping," DYSIS, 2021, available at http://dysismedical.com/wp-content/uploads/2021/07/0354-01248-DYSIS-Ultra-Brochure-R3.pdf.
"EVA System, Digital innovation for colposcopy," MobileODT, 2019, available at https://www.mobileodt.com/products/eva-colpo/?doing_wp_cron=1654899822.7874989509582519531250.

(Continued)

*Primary Examiner* — Alexandra L Newton
(74) *Attorney, Agent, or Firm* — Nelson IP; Daniel P. Nelson (57) ABSTRACT

An apparatus for diagnosing and treating cervical precancer includes a handheld colposcope comprising a camera and screen configured to view and generate an image of a cervix. A thermal ablation probe is incorporated into the handheld colposcope and is configured to apply heat to the cervix in response to detection of cervical precancer by the handheld colposcope. In certain embodiments, a lens of the camera is positioned to visually assist in placing the thermal ablation probe onto the cervix. In certain embodiments, the handheld colposcope is further configured to recognize, using artificial intelligence or other algorithms, one or more of the cervix in the image, whether the cervix comprises precancerous lesions, and the stage of any precancer. A corresponding method is also disclosed.

20 Claims, 10 Drawing Sheets

(56) References Cited

OTHER PUBLICATIONS

"Cervaical Mobile Colposcope. Making Cervical Exams Smarter, Easier & More Affordable For All," UE LifeSciences 2019, available at https://www.uelifesciences.com/cervaical.
"The Gynocular," Gynius, 2020, available at: https://gynius.se/gynocular.
"The Pocket Colposcope," Calla Health Foundation, 2022, available at https://callahealthfoundation.com/pocket-colposcope/.
"Continuous Zoom Colposcopes—Exceptional Optics and Performance," Wallach, 2018 available at https://www.coopersurgical.com/product-resources/d09810c9-bae2-472a-97df-c8a69b1d29ae_Wallach-Colposcope-Sell-Sheet2.pdf.
"Smart Scope," Periwinke Technologies, available at https://www.periwinkletech.com/smart-scope/, date unknown.
LT-300 SD/LT-300 HD High Definition Digital Video Colposcope, Lutech, available at https://www.lutechmedical.com/wp-content/uploads/2021/07/LT-300-SD-HD-Brochure-V2-190123A.pdf (date unknown).
Ferris, Daron, et al., "Colposcopes: A Critical Review," The Journal of Family Practice, vol. 33, No. 5, 1991.
Fusco, Eugenio, et al., "History of Colposcopy: A Brief Biography of Hinselmann," Journal of Prenatal Medicine, 2008.
"MedGyn AL-101 Colposcope," MedGyn, available at https://www.compressionmedical.com/content/MedGyn%20AL-101%20Colposcope.pdf (date unknown).
"Low Cost Pocket Colposcope Could Be Future of Cervical Cancer Screening," Duke Innovations, Jan. 2019. available at https://otc.duke.edu/news/low-cost-pocket-colposcope/#:~:text=Low%20Cost%20Pocket%20Colposcope%20Could%20Be%20Future%20of%20Cervical%20Cancer%20Screening,-Developed%20by%20Duke.

\* cited by examiner

COLPOSCOPE WITH INTEGRATED PATIENT MANAGEMENT AND THERMAL ABLATION FUNCTIONALITY

BACKGROUND

Field of the Invention

This invention relates to apparatus and methods for diagnosing and treating cervical precancer.

Background of the Invention

Cervical cancer is one of the gravest threats to the lives of women around the world. Globally, one woman dies of cervical cancer every two minutes. However, cervical cancer is one of the most preventable and treatable forms of cancer as long as it is prevented with HPV vaccination, screening and treatment of cervical precancer lesions, and effective management of cervical precancer.

Persistent infection of the cervix with "high risk" genotypes of human papillomavirus (HPV) is the major cause of precancerous lesions, which can lead to invasive cervical cancer if they are not treated. According to GLOBOCAN 2018, 311,000 women die of cervical cancer each year, with eighty-five percent of them in less developed regions of the world. Progression to cancer usually takes many years, which gives clinicians an opportunity for early detection and time to treat lesions when they are found during screening.

Because of the large number of preventable cervical-cancer-related deaths that occur each year, a "call to action" was made by Dr. Tedros Adhanom Ghebreyesus, Director General of the World Health Organization, in May of 2018. This has resulted in accelerating plans to meet the challenge of improving cancer control under the elimination threshold in terms of cervical cancer incidence. Achieving this elimination of cervical cancer will require collective efforts of countries and partner organizations to ensure that effective interventions reach the majority of all girls and women. For this elimination initiative to be effective, it must be conducted in a manner in which all core challenges are specifically and comprehensively approached.

In order to prevent cervical-cancer-related deaths, tools are needed to effectively screen girls and women for cervical precancer lesions, as well as treat cervical precancer lesions when they are discovered. Ideally, such tools will be portable and capable of effectively screening and/or treating large numbers of patients quickly and reliably. Such a tool would also ideally require minimal training and be tailored to low-resource settings commonly encountered in less developed parts of the world.

SUMMARY

The invention has been developed in response to the present state of the art and, in particular, in response to the problems and needs in the art that have not yet been fully solved by currently available apparatus and methods. Accordingly, apparatus and methods have been developed to effectively diagnose and treat cervical precancer. The features and advantages of the invention will become more fully apparent from the following description and appended claims, or may be learned by practice of the invention as set forth hereinafter.

Consistent with the foregoing, an apparatus for diagnosing and treating cervical precancer is disclosed. In one embodiment, such an apparatus includes a handheld colposcope comprising a camera and screen configured to view and generate an image of a cervix. A thermal ablation probe is removably incorporated into the handheld colposcope and is configured to apply heat to the cervix in response to detection of cervical precancer by the handheld colposcope. In certain embodiments, a lens of the camera is positioned to visually assist in placing the thermal ablation probe onto the cervix. Similarly, in certain embodiments, the handheld colposcope is configured to recognize, using artificial intelligence or other algorithms, the cervix in the image as well as recognize whether the cervix comprises precancerous lesions and potentially the stage of the precancer. This information may be used by the handheld colposcope to manage treatment of a patient as well as determine whether the built-in thermal ablation probe would be helpful in treating the precancerous lesion.

A corresponding method is also disclosed and claimed herein.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

It will be readily understood that the components of the present invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

The present invention may be embodied as a system, method, and/or computer program product. The computer program product may include a computer readable storage medium (or media) having computer readable program instructions thereon for causing a processor to carry out aspects of the present invention.

The computer readable storage medium may be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages.

The computer readable program instructions may execute entirely on a user's computer, partly on a user's computer, as a stand-alone software package, partly on a user's computer and partly on a remote computer, or entirely on a remote computer or server. In the latter scenario, a remote computer may be connected to a user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, may be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus, or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other implementations may not require all of the disclosed steps to achieve the desired functionality. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

As previously mentioned, in order to prevent cervical-cancer-related deaths, tools are needed to effectively screen girls and women for cervical precancer lesions, as well as treat cervical precancer lesions when they are found. Such tools will ideally be portable and capable of effectively screening and/or treating large numbers of patients quickly and reliably. Such tools would also ideally require minimal training and be tailored to low-resource settings commonly encountered in less developed parts of the world.

Figure 1:
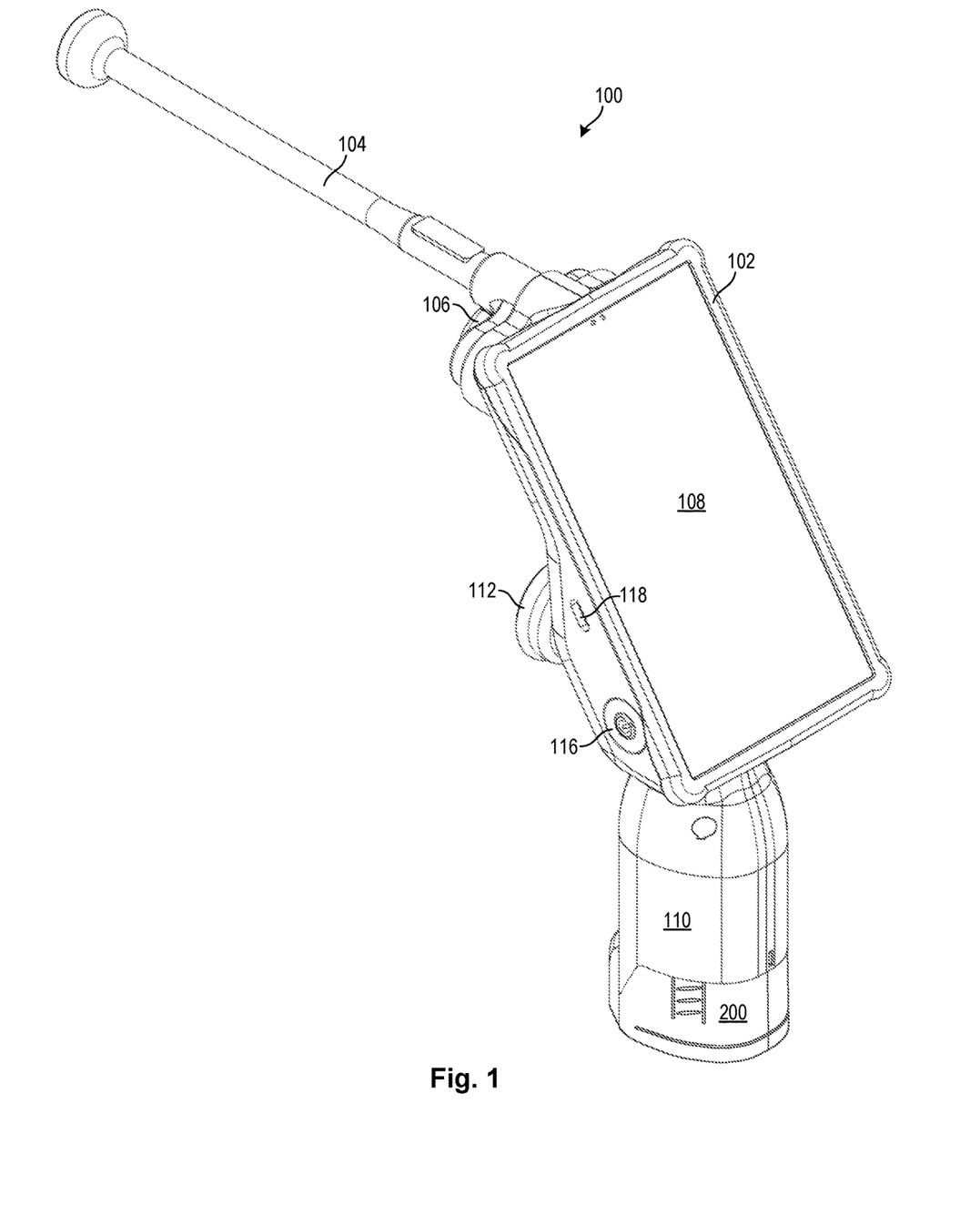
FIG. 1 is a perspective view of one embodiment of a handheld colposcope comprising an integrated thermal ablation probe.
Figure 2:
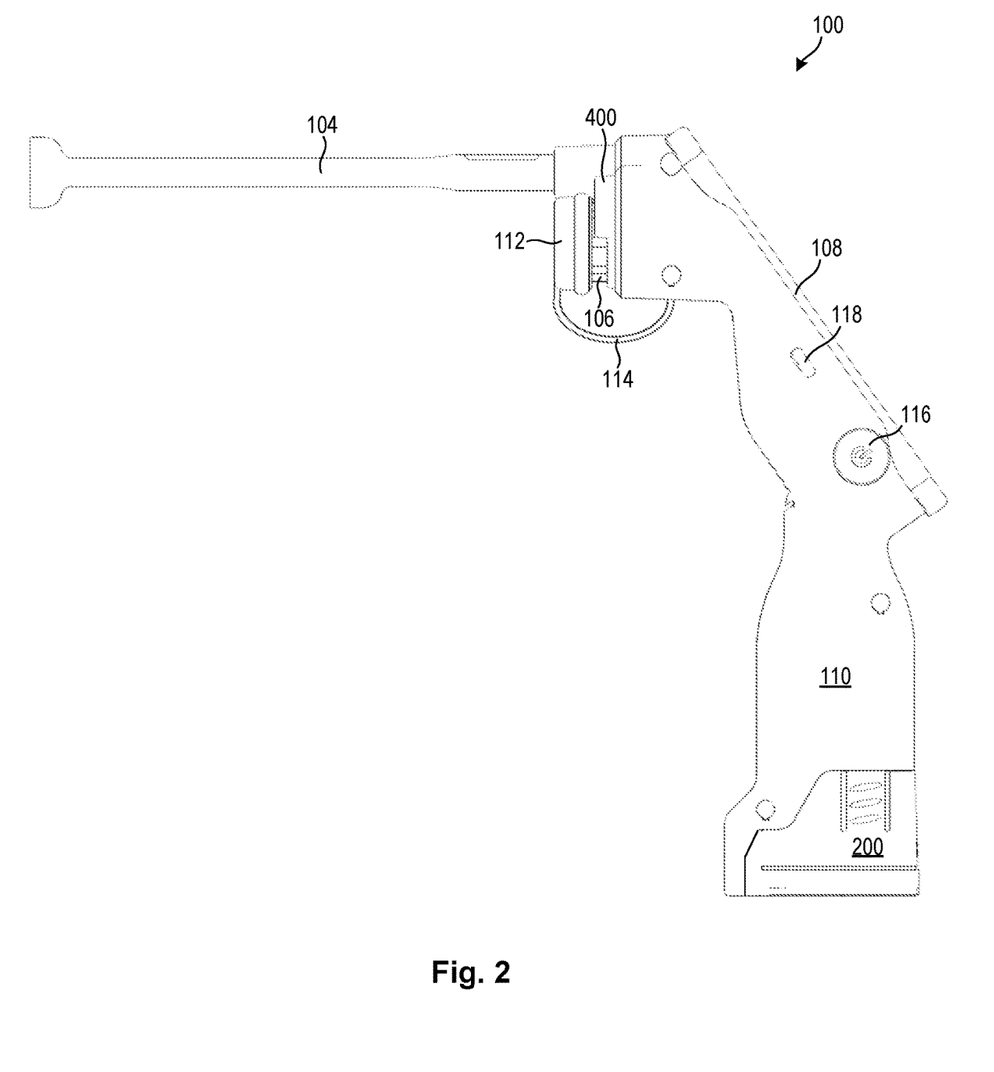
FIG. 2 is a side view of the handheld colposcope with integrated thermal ablation probe shown in FIG. 1.
Figure 3:
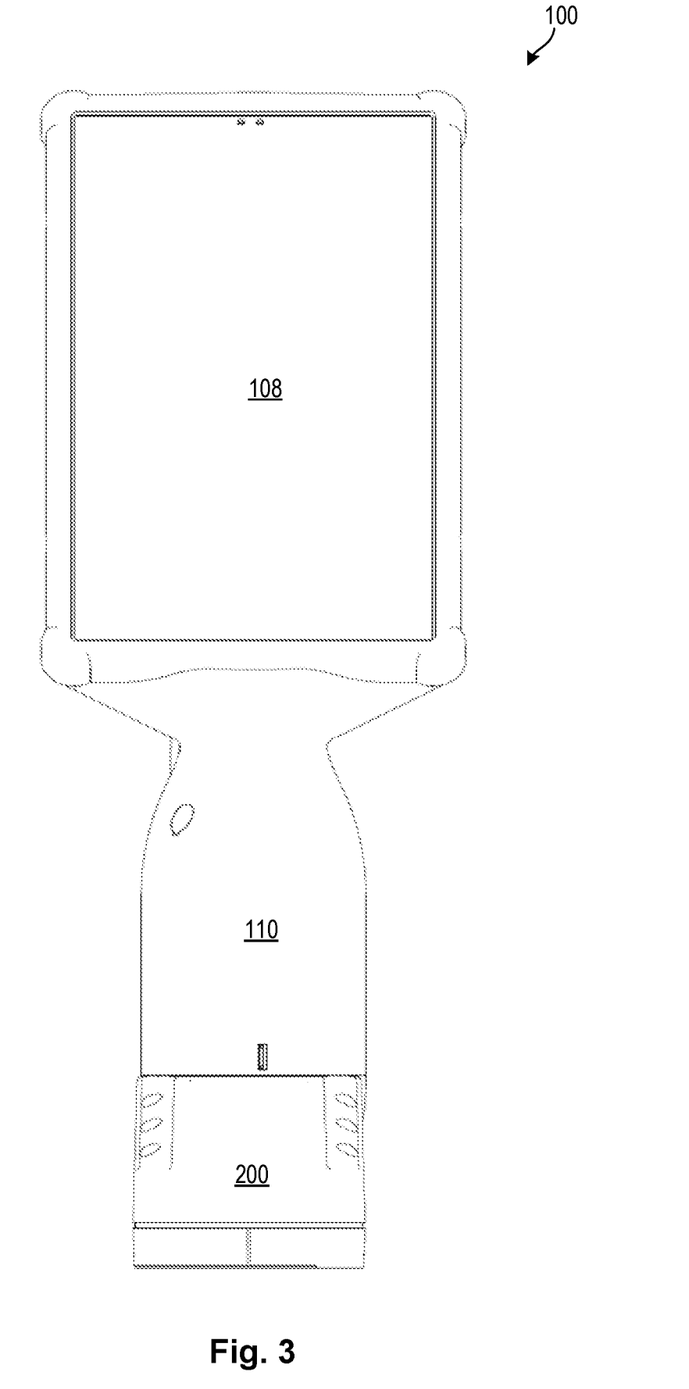
FIG. 3 is a rear view of the handheld colposcope with integrated thermal ablation probe shown in FIG. 1.

Referring now to FIGS. 1 through 5, various views of one embodiment of an apparatus 100 for diagnosing and treating precancerous lesions are illustrated. FIG. 1 shows a perspective of the apparatus 100. FIGS. 2 through 5 show various other views of the apparatus 100, some with the battery 200 installed and others with the battery 200 removed, from the side, rear, front, and top.

As shown in FIGS. 1 through 5, the apparatus 100 provides a handheld colposcope 102 with a removably integrated thermal ablation probe 104. As will be explained in more detail hereafter, the integration of the thermal ablation probe 104 with the handheld colposcope 102, as well as integrated functionality for automatically recognizing a cervix and precancerous lesions, along with functionality to recommend various treatment modalities, provide synergistic advantages and benefits that are not provided by separate colposcopes and thermal ablation devices. The end result is an apparatus 100 that is much more useful, reliable, and comprehensive in diagnosing, managing, and treating precancerous lesions that are discovered on a cervix.

As shown, the handheld colposcope includes a camera 106 and screen 108 (such as a touchscreen 108) for viewing and magnifying a cervix, as well as viewing and inputting information. In certain embodiments, the screen 108 is provided at an angle of around 45-60 degrees relative to a line of sight of the camera 106 to provide an optimal viewing angle to a user when performing examinations (with the thermal ablation probe 104 removed) or performing treatment with the thermal ablation probe 104 (with the thermal ablation probe 104 installed). A power button 116 may be provided to turn the apparatus 100 on or off and a USB port 118 may be provided to transfer data to or from the apparatus 100 as well as potentially charge the apparatus 100.

The camera 106 may be controlled by special hardware and software as will explained in more detail hereafter. In certain embodiments, the camera 106 includes an image sensor that is configured to take an exposure at a fast shutter speed (e.g., 8 msec.) to minimize motion blur of the cervix. One or more lights 400, such as light-emitting diodes (LEDs) 400, may be placed near a lens 402 of the camera 106. These lights 400 may be strobed at high intensity to illuminate the cervix and yield an optimal image with minimal noise artifacts. In certain embodiments, multiple lights 400 may be provided on opposing sides of the camera lens 402 to reduce shadows in the resulting image. Lenses of the lights 400 and/or camera 106 may be polarized to reduce or eliminate glare. Similarly, lenses of the lights 400 may be convex to concentrate light onto the cervix instead of on the perineum or other areas of the patent. A cover 112 and associated flexible tether 114 may be provided to cover a lens of the camera 106 when not in use or when the apparatus 100 is stored.

A cervical image generated by the camera 106 may be analyzed by the apparatus 100 to recognize the cervix, any precancerous lesions on the cervix, as well as the stage of any precancerous lesions. In certain embodiments, the apparatus 100 may recommend a course of treatment based on this information. In certain embodiments, the colors of the cervical image that is generated by the camera 106 are unenhanced in order to more accurately display cervical tissue. One disadvantage of using different types of colposcopes to diagnose precancerous lesions is that the images generated by these colposcopes may differ significantly in color, clarity, lighting, resolution, and the like. This may affect the diagnosis of precancerous lesions and the recommended treatment. By incorporating a thermal ablation probe 104 (i.e., a treatment device) with a handheld colposcope 102 (i.e., a diagnosis device), utilization of the treatment device is based on diagnosis and images received from a closely paired diagnosis device, thereby providing a more reliable recommended course of treatment and actual treatment.

Figure 4:
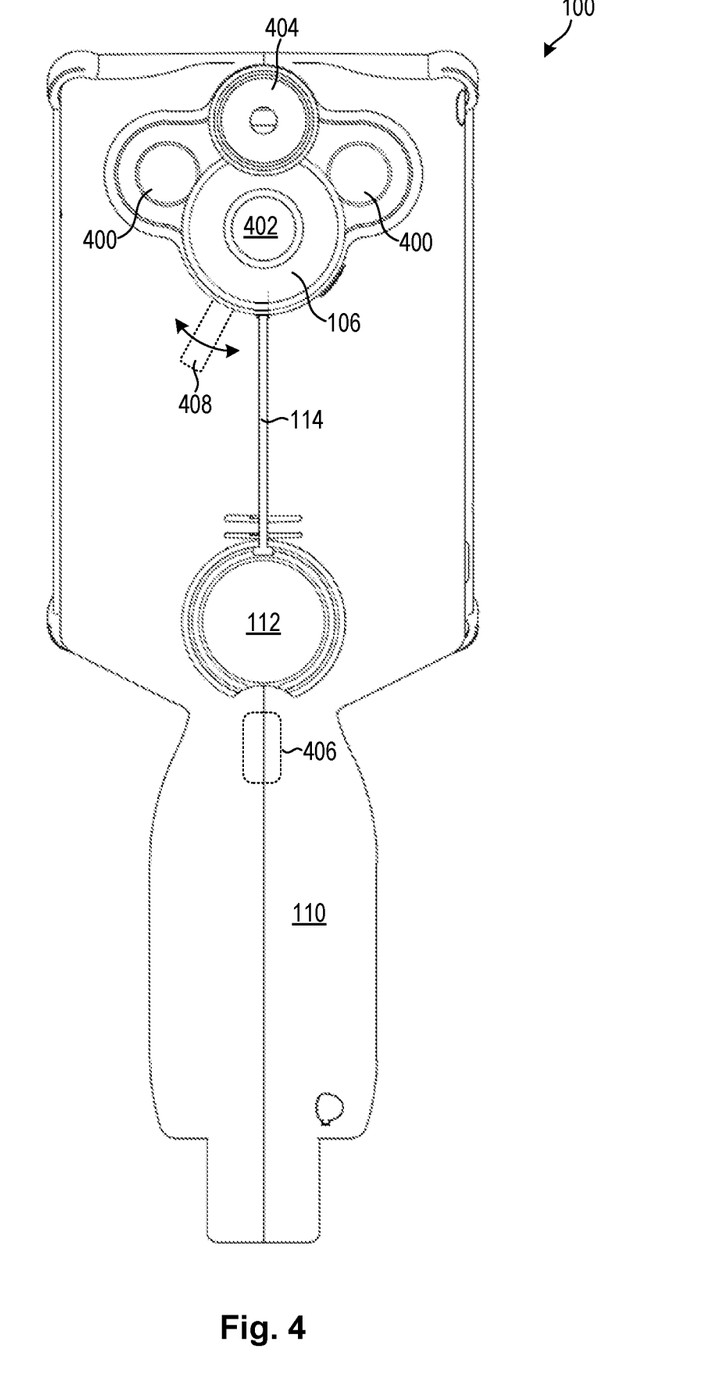
FIG. 4 is a front view of the handheld colposcope with integrated thermal ablation probe shown in FIG. 1.
Figure 5:
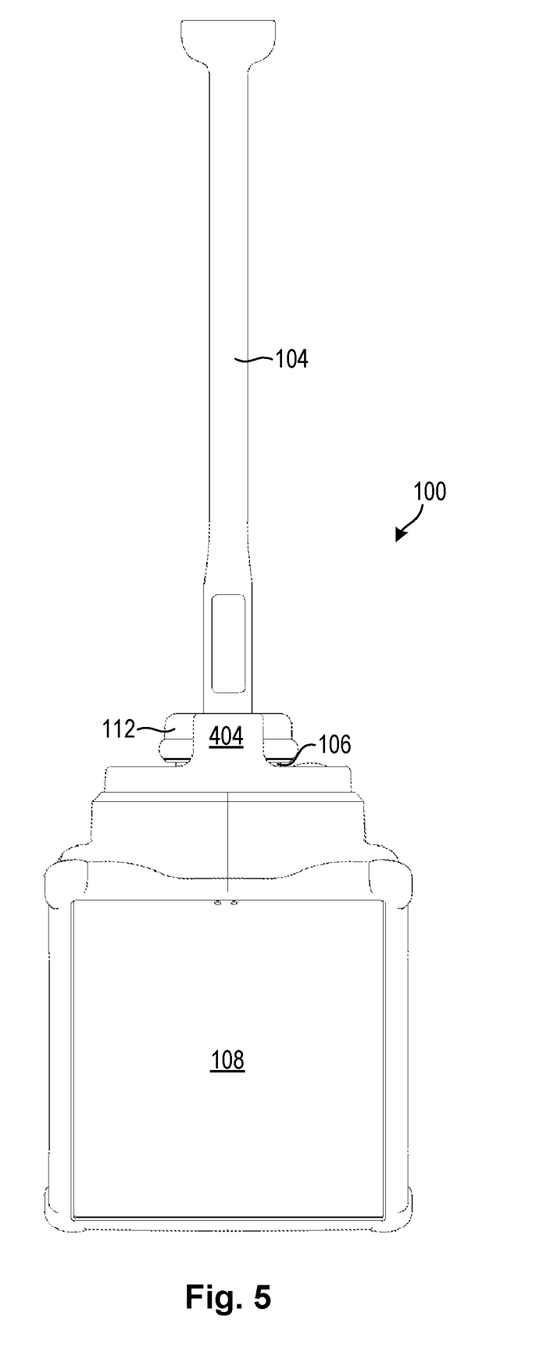
FIG. 5 is a top view of the handheld colposcope with integrated thermal ablation probe shown in FIG. 1.

In certain embodiments, a focal length of the camera 106 is set between ten and forty centimeters for a full cervical view (the cervix is typically 3-5 centimeters in diameter) and provide optimal resolution. In certain embodiments, the camera includes a smaller aperture (e.g., f/11.2) to maximize a depth of field and provide optimal image clarity. Similarly, in certain embodiments, the camera 106 is configured to be manually focused to assure proper focus of the camera 106 on the cervix rather than on other areas such as pubic hairs or instruments such as a speculum. For example, as shown in FIG. 4, in certain embodiments, a lever 408 may be provided below a lens 402 of the camera 106. This lever 408 may be pushed or rotated with a thumb or other finger relative to the lens 402, as indicated by the arrow, to manually focus the camera 106. The position and operation of the lever 408 may also prevent a user's thumb or finger from interfering with the view of the camera 106 or blocking the lights 400 when manually focusing the camera 106.

In certain embodiments, a trigger 406 may be provided on the apparatus 100 to cause the camera 106 to take an image. Alternatively, or additionally, the trigger 406 may be used to activate heating of the thermal ablation probe 104 when installed in the apparatus 100. The trigger 406 may reduce or minimize movement of the apparatus 100 when taking an image or activating the thermal ablation probe 104. In certain embodiments, the trigger 406 is one of several options for taking an image with the apparatus 100. For example, the apparatus 100 may also be configured to take an image using one or more of an icon on the screen 108, a proximity sensor to detect a hand wave, a Bluetooth mouse or shutter button, a Bluetooth foot pedal to take an image or to zoom in or out on an image, or the like.

In the event the cervix is diagnosed with precancerous lesions, the thermal ablation probe 104 may be utilized to thermally ablate tissue on the cervix. As shown in the Figures, the thermal ablation probe 104 is removeable from the apparatus 100. This allows the thermal ablation probe 104 to be removed from the apparatus 100 when the colposcope is in use and installed in the apparatus 100 when the thermal ablation probe 104 is needed. This also allows different types and shapes of thermal ablation probes 104 to be installed in the apparatus 100 depending on the treatment that is needed and/or the shape/size/condition of the patient's cervix. As shown in FIG. 4, a socket 404 may be provided in the apparatus 100 to receive the thermal ablation probe 104.

One benefit of incorporating the thermal ablation probe 104 with the handheld colposcope 102 is that the camera 106 that is used for examining the cervix and taking images may be used for a secondary purpose as it relates to the thermal ablation probe 104. When the thermal ablation probe 104 is installed in the apparatus 100 to thermally ablate cervical tissue, the camera 106 and screen 108 may secondarily be used by a healthcare provider to accurately direct the thermal ablation probe 104 onto the cervix. Similarly, the lights 400 that are used in association with the camera 106 to view the cervix or take an image may also be used secondarily to illuminate the cervix and thereby assist a healthcare provider in accurately placing the thermal ablation probe 104 thereon. To provide this benefit, the camera 106 and/or lights 400 may, in certain embodiments, be placed proximate the thermal ablation probe 104 when installed in the apparatus 100, such as within several inches (e.g. two inches) of the thermal ablation probe 104 or associated socket 404, to provide viewing and/or lighting of the cervix or other areas of the patient's anatomy at an angle that is satisfactory. In certain embodiments, the camera 106 is within three inches of the thermal ablation probe 104. In other embodiments, the camera 106 is within two inches of the thermal ablation probe 104. In yet other embodiments, the camera 106 is within one inch of the thermal ablation probe 104. Thus, the integration of the thermal ablation probe 104 with the colposcope 102 may provide some synergistic benefits where various features and functionality may advantageously serve multiple purposes.

The combined colposcope 102 and thermal ablation probe 104 provides a significantly more useful tool in screening and treating women for pre-cervical cancer compared to tools currently available in the market or currently under development of which the inventor of the apparatus 100 is aware. The tool is very portable and eliminates other more bulky and cumbersome tools. Because of these advantages, the tool has the potential to be much more useful in the field, particularly in developing or third-world countries that are very resource-constrained. The resulting apparatus 100 is a very effective tool that has the potential to save many lives. As shown in FIGS. 1 through 5, the apparatus 100 may be configured with a handle 110 to facilitate holding and manipulation by a healthcare provider. In the illustrated embodiment, the battery 200 is configured to plug into this handle 110. The removability of the battery 200 allows a new or charged battery 200 to be swapped into the apparatus 100 and allows the removed battery 200 to be charged apart from the apparatus 100. In some embodiments, functionality may be provided to enable the battery 200 to charge while installed in the apparatus 100.

Figure 6:
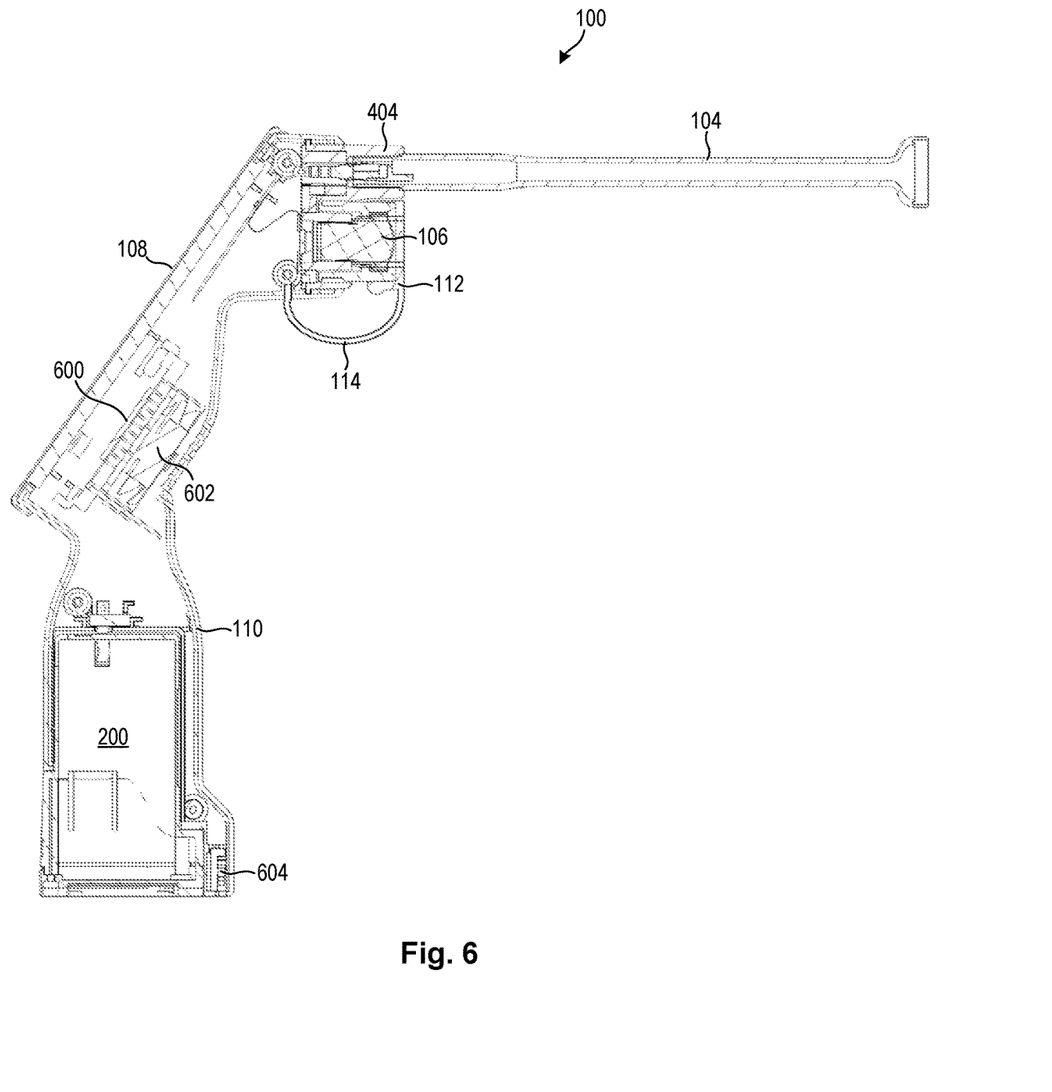
FIG. 6 is a cross-sectional side view of the handheld colposcope with integrated thermal ablation probe shown in FIG. 1.
Figure 7:
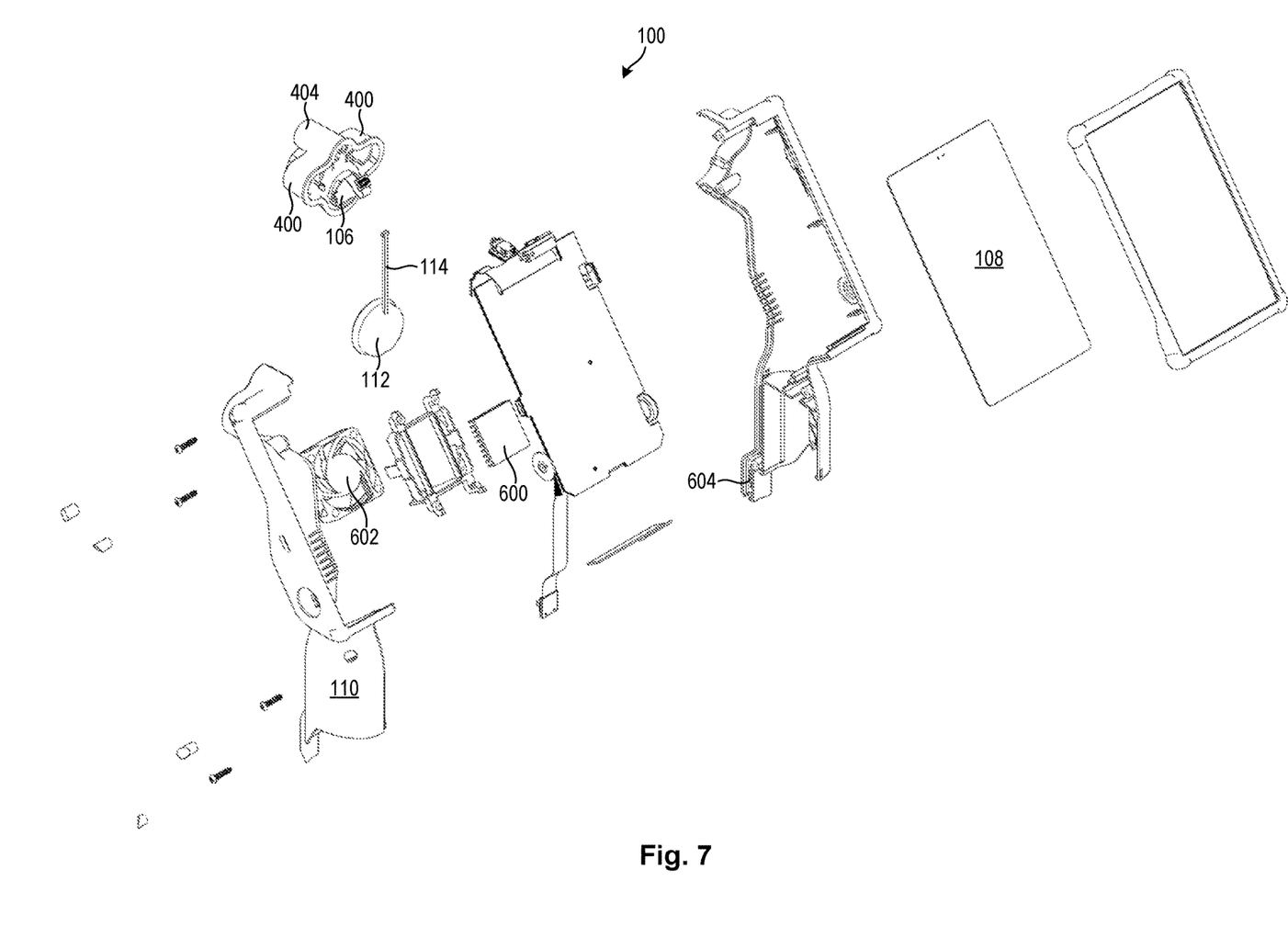
FIG. 7 is an exploded perspective view of the handheld colposcope with integrated thermal ablation probe shown in FIG. 1.

FIG. 6 is a cross-sectional side view and FIG. 7 is an exploded perspective view of the apparatus 100 of FIGS. 1 through 5. Some notable components that are not visible in FIGS. 1 through 5 include a microprocessor 600 (i.e., CPU 600) that contains data processing logic for the apparatus 100 and executes an application for performing tasks such as analyzing images of the cervix to recognize the cervix, precancerous lesion, and/or the stage of the precancer, generating a treatment plan or recommendations depending on what is discovered, and operating the thermal ablation probe 104. This application will be discussed in more detail in association with FIG. 10. As further shown, a fan 602 may be provided to cool the microprocessor 600 as well as other components within the apparatus 100. Other features of the apparatus 100 that are not readily visible in the Figures may include a speaker to inform a user of different issues with the apparatus 100, and a microphone to input information.

In certain embodiments, a video port 604, such as an HDMI port, may be incorporated into the apparatus 100. This video port 604 may enable a cable to be connected to the apparatus 100 to relay cervical video/images from the apparatus 100 to an external monitor or viewing device. This may be used for teaching or training a patient or healthcare worker, such as showing cervical lesions and what steps need to be performed to remove precancerous tissue. The video/images may be helpful not only in diagnosing cervical precancer, but also showing treatment of the cervix with the thermal ablation probe 104. In other or the same embodiments, wireless functionality may be incorporated into the apparatus 100 to wirelessly relay video/images to an external monitor or device.

Figure 8:
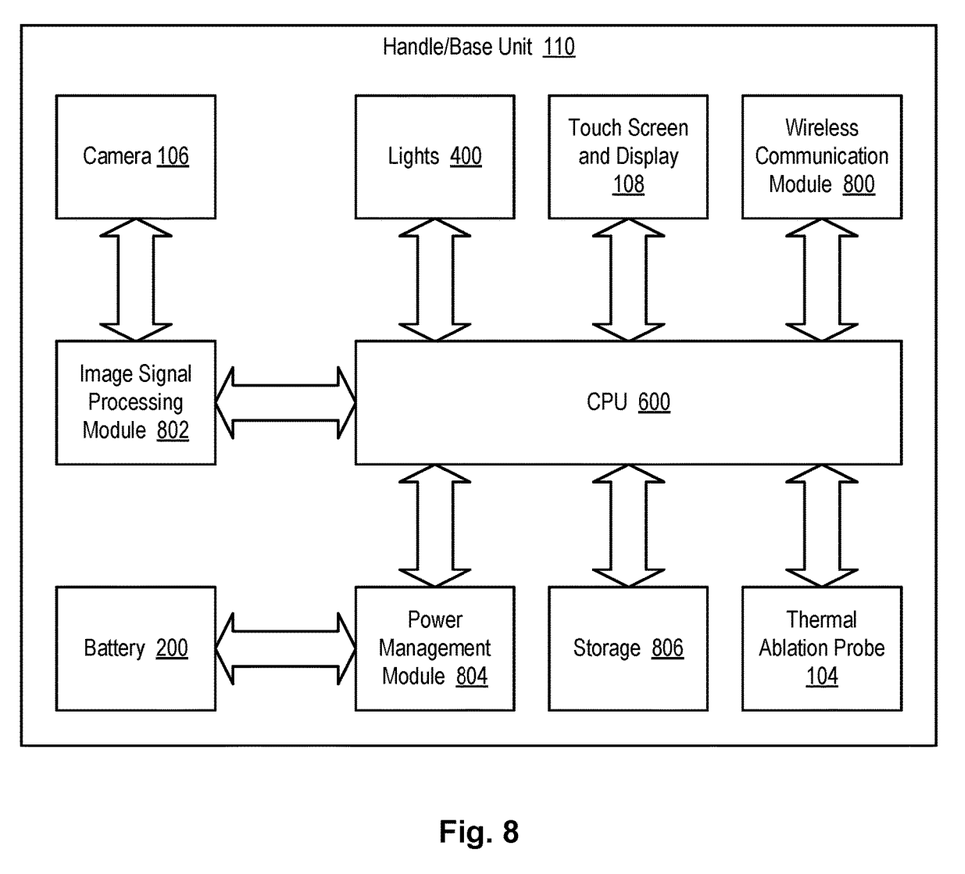
FIG. 8 is a high-level block diagram showing hardware that may be included in the handheld colposcope with integrated thermal ablation probe of FIG. 1.

FIG. 8 is a high-level block diagram showing hardware that may be included in the apparatus 100. As shown, the apparatus 100 may include a processor 600 for providing data processing logic. In certain embodiments, the processor 600 is a system on a chip (SoC) that contains different components, such as I/O ports, internal memory, video processing, graphics processing, neural processing units (NPUs) optimized for machine-learning and artificial intelligence, and the like. As shown, the processor 600 interfaces with various components in the apparatus 100 by way of various ports, buses, or communication interfaces, such as the camera 106, lights 400, touch screen 108, and thermal ablation probe 104 as previously discussed. The processor 600 may also interface with a wireless communication module 800 to enable the apparatus 100 to wirelessly communicate with external systems, devices, or networks using a communication protocol such as WiFi, Bluetooth, cellular communication protocols, or the like. The processor 600 may also interface with external storage 806 to store information such as patient information, medical records, images, etc.

In certain embodiments, the processor 600 interfaces with a power management module 804 that is configured to manage power from a battery 200 and provide power to various components of the apparatus 100. Among other tasks, the power management module 804 may manage output, charging, and discharging of the battery 200, as well as provide notifications on the status of the battery 200.

As further shown, the processor 600 interfaces with an image signal processing module 802 that is configured to receive and process image data received from the camera 106. Among other tasks, the image signal processing module 802 may perform tasks such as demosaicing, noise reduction, auto exposure, auto focus, auto white balance, and the like. In certain embodiments, the image signal processing module 802 may also be configured to perform or assist with more advanced tasks, such recognizing a cervix in an image, recognizing precancerous lesions on the cervix, and/or recognizing a stage of precancer on the lesions.

Figure 9:
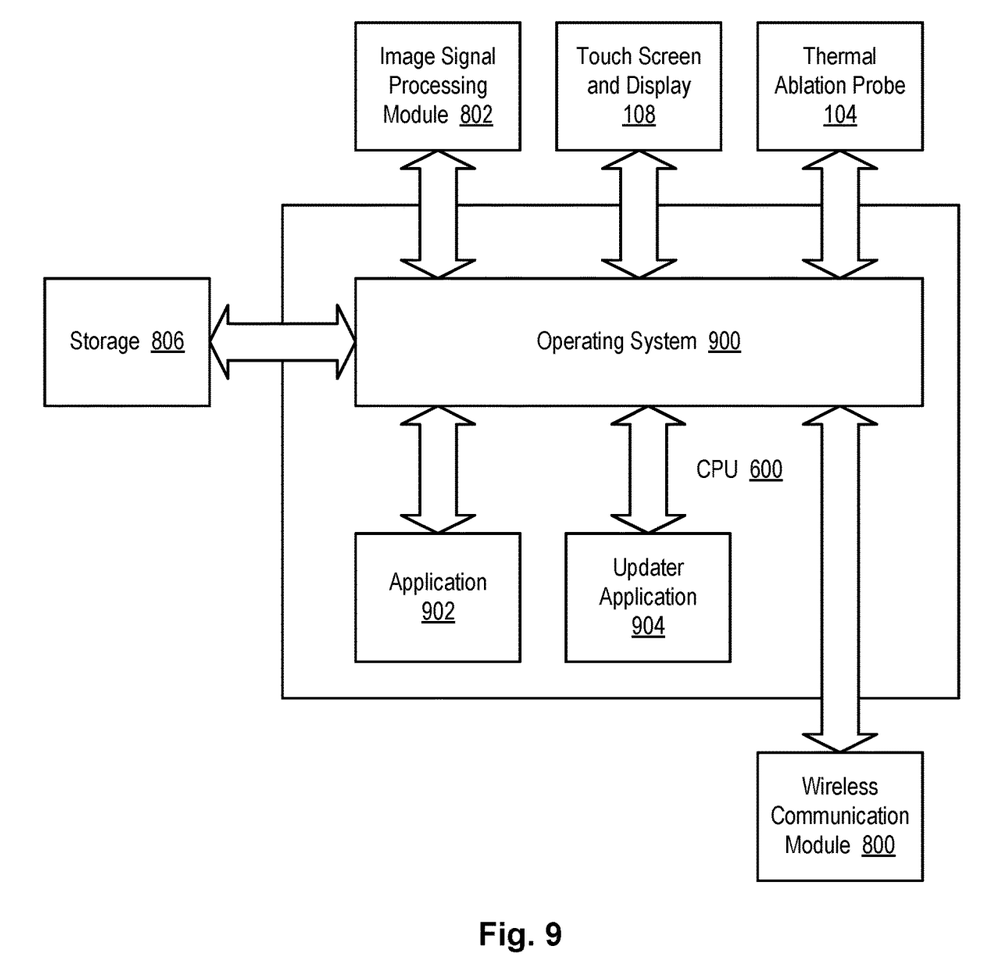
FIG. 9 is a high-level block diagram showing software/firmware that may be included in the handheld colposcope with integrated thermal ablation probe of FIG. 1.

FIG. 9 is a high-level block diagram showing software/firmware that may be utilized in the apparatus 100. As shown, the processor 600 may host an operating system 900, an application 902, and an updater application 904. The operating system 900, which in certain embodiments may be the Android operating system 900, may manage software and hardware on the apparatus 100. Thus, as shown in FIG. 9, the operating system 900 may provide an interface between an application 902 and various hardware of the apparatus 100, such as the thermal ablation probe 104, touch screen 108, image signal processing module 802, storage 806, and wireless communication module 800 previously discussed. An updater application 904 may keep the application 902 updated with any fixes or improvements. In certain embodiments, these updates are provided over the air.

Figure 10:
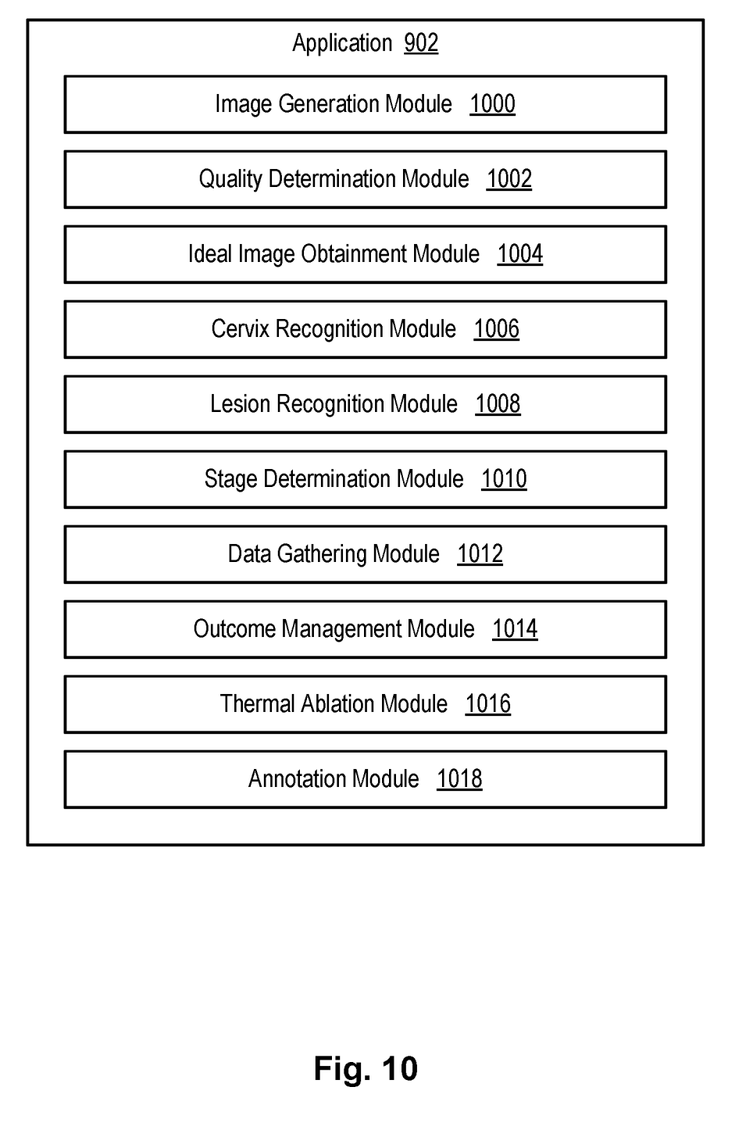
FIG. 10 is a high-level block diagram showing an application and various sub-modules that may be tailored to the handheld colposcope with integrated thermal ablation probe of FIG. 1.

Referring to FIG. 10, a high-level block diagram showing the application 902 and various associated sub-modules within the application is illustrated. The application 902 and associated sub-modules are presented by way of example and not limitation. More or fewer sub-modules may be provided in different embodiments. For example, the functionality of some sub-modules may be combined into a single or smaller number of sub-modules, or the functionality of a single sub-module may be distributed across several sub-modules.

As shown, in certain embodiments, the application 902 includes one or more of an image generation module 1000, quality determination module 1002, ideal image obtainment module 1004, cervix recognition module 1006, lesion recognition module 1008, stage determination module 1010, data gathering module 1012, outcome management module 1014, thermal ablation module 1016, and annotation module 1018.

During operation of the colposcope, the image generation module 1000 may, using the camera 106, be configured to generate an image of a cervix. The quality determination module 1002 may be configured to determine the quality of this image. Determining the quality may include for example, determining whether the image is in focus, has minimal noise artifacts, and has acceptable detail, color, and lighting. Determining the quality may also include determining whether the characteristics of the image are adequate for artificial intelligence to perform various tasks on the image, such as recognizing the cervix, recognizing precancerous lesions on the cervix, and recognizing the stage of any precancer that is discovered. If the quality is acceptable, the ideal image obtainment module 1004 may obtain an ideal image of the cervix for analysis.

Once the ideal image is obtained, the cervix recognition module 1006 may analyze the ideal image to identify the cervix within the image. In certain embodiments, this may include outlining the cervical area. In the same or different embodiments, this may include identifying and/or outlining the squamous columnar junction (SCJ) of the cervix. In certain embodiments, the cervix recognition module 1006 accomplishes this using artificial intelligence, and more particularly by utilizing a neural network that has been trained to recognize a cervix and/or the SCJ in an image. In other embodiments, non-neural approaches to recognizing the cervix may also be used.

In a similar manner, once a cervix has been recognized in the image, the lesion recognition module 1008 may recognize whether any precancerous lesions are present on the cervix, including potentially outlining or otherwise indicating where the precancerous lesions are located on the cervix. In certain embodiments, artificial intelligence that has been trained with precancer-containing images may be used to make this determination. In the event any precancerous lesions are discovered on the cervix, the stage determination module 1010 may determine the stage of the precancer. This may also be accomplished using artificial intelligence that has been trained in the manner described above.

The data gathering module 1012 may be used to collect information (e.g. HPV test results indicating whether the patient was determined to have a genotype of the HPV virus that is known to cause cancer, previous treatment received by the patient, etc.) on a patient that is associated with an image. Using this gathered information as well as determinations made by the lesion recognition module 1008 and stage determination module 1010, the outcome management module 1014 may manage the patient for optimal outcome and determine a course of treatment for any identified precancerous lesions. In the event the determined course of treatment includes performing thermal ablation on the cervix, the thermal ablation module 1016 may be used to activate and control operation of the thermal ablation probe 104 once it has been installed in the apparatus 100. This may include controlling the temperature of a heating element at an end of the thermal ablation probe 104 as well as the time that the heating element is energized. The thermal ablation probe 104 may then be used to ablate the precancerous tissue on the patient's cervix.

The annotation module 1018 may enable a user to annotate a cervical image either before or after thermal ablation is administered to the cervix. In certain embodiments, the annotation module 1018 may enable drawings, text, or symbols to be added to cervical images. This may assist in documenting a diagnosis of cervical precancer and treatment of the precancer. In certain embodiments, images may be saved in association with a selected patient to provide records with respect to the patient's diagnosis and/or treatment.

One advantage of having artificial intelligence (e.g., image recognition technology) integrated into the apparatus 100 is that the artificial intelligence (and associated neural networks) may be trained using images generated by the apparatus 100, or a similarly configured apparatus 100. This ensures that images that are used to train the artificial intelligence are generated by the same device as the images that are being processed by the image recognition technology. This may improve the accuracy of the artificial intelligence in recognizing a cervix, precancerous lesions on the cervix, as well as a stage of any precancer on the cervix. In certain embodiments, biopsies of precancerous lesions may be taken and sent for gold-standard histologic pathology diagnosis, which can be used to further train and refine the accuracy of the artificial intelligence algorithm utilized by the apparatus 100.

In the above disclosure, reference has been made to the accompanying drawings which is shown by way of illustration specific implementations in which the disclosure may be practiced. It is understood that other implementations may be utilized and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

While various embodiments of the present disclosure have been described above, it should be understood that they have been presented by way of example only and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments, but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teachings. Further, it should be noted that any or all of the aforementioned alternate implementations may be used in any combination desired to form additional hybrid implementations of the disclosure.

The invention claimed is:

1. An apparatus for diagnosing and treating cervical precancer, the apparatus comprising:
a handheld colposcope comprising a camera and screen configured to view and generate an image of a cervix of a patient; and
a thermal ablation probe removably integrated into the handheld colposcope and configured to apply heat to the cervix in response to detection of precancerous lesions on the cervix, wherein the camera and thermal ablation probe are positioned relative to one another such that a lens of the camera resides outside a body of the patient when the thermal ablation probe is in contact with the cervix.

2. The apparatus of claim 1, wherein the lens of the camera is positioned to visually assist in placing the thermal ablation probe onto the cervix.

3. The apparatus of claim 1, wherein the lens of the camera is positioned less than two inches away from the thermal ablation probe.

4. The apparatus of claim 1, wherein the handheld colposcope is further configured to recognize the cervix in the image using a neural network that has been trained to recognize a cervix within an image.

5. The apparatus of claim 4, wherein the handheld colposcope is further configured to recognize whether the cervix comprises a precancerous lesion using a neural network that has been trained with pre-cancer containing images to recognize precancer on a cervix.

6. The apparatus of claim 5, wherein the handheld colposcope is further configured to determine a stage of the precancerous lesion using a neural network that has been trained with pre-cancer containing images to recognize a stage of precancer on a cervix.

7. The apparatus of claim 6, wherein the handheld colposcope is further configured to invoke an outcome management module that is configured to determine a course of treatment for the precancerous lesion based on recognition of the following within a cervical image: the cervix; any precancerous lesions on the cervix; and a stage of any precancerous lesions on the cervix.

8. The apparatus of claim 1, wherein the handheld colposcope comprises at least one light positioned proximate a lens of the camera and configured to direct light onto the cervix.

9. The apparatus of claim 8, wherein the handheld colposcope comprises multiple lights on opposing sides of the lens to reduce shadows on the cervix.

10. The apparatus of claim 1, wherein the thermal ablation probe is removeable from a socket of the handheld colposcope.

11. A method for diagnosing and treating cervical precancer, the method comprising:
viewing and generating an image of a cervix of a patient using a handheld colposcope comprising a camera and screen; and
applying heat to the cervix using a thermal ablation probe that is removably integrated into the handheld colposcope and configured to apply heat to the cervix in response to detection of precancerous lesions on the cervix, wherein the camera and thermal ablation probe are positioned relative to one another such that a lens of the camera resides outside a body of the patient when the thermal ablation probe is in contact with the cervix.

12. The method of claim 11, further comprising using the lens of the camera to visually assist in placing the thermal ablation probe onto the cervix.

13. The method of claim 12, wherein the lens of the camera is positioned less than two inches away from the thermal ablation probe.

14. The method of claim 11, further comprising recognizing, using a neural network that has been trained to recognize a cervix within an image, the cervix in the image.

15. The method of claim 14, further comprising recognizing, using a neural network that has been trained with pre-cancer containing images to recognize precancer on a cervix, whether the cervix comprises a precancerous lesion.

16. The method of claim 15, further comprising determining, using a neural network that has been trained with pre-cancer containing images to recognize a stage of pre-cancer on a cervix, a stage of the precancerous lesion.

17. The method of claim 16, further comprising invoking an outcome management module that is configured to determine a course of treatment for the precancerous lesion based on recognition of the following within a cervical image: the cervix; any precancerous lesions on the cervix; and a stage of any precancerous lesions on the cervix.

18. The method of claim 11, further comprising directing light onto the cervix using at least one light incorporated into the handheld colposcope and positioned proximate the lens of the camera.

19. The method of claim 18, further comprising directing light onto the cervix using multiple lights on opposing sides of the lens to reduce shadows on the cervix.

20. The method of claim 11, further comprising enabling removal of the thermal ablation probe from a socket of the handheld colposcope.

* * * * *